United States Patent
Abuzaina et al.

(10) Patent No.: US 8,753,361 B2
(45) Date of Patent: Jun. 17, 2014

(54) BIOCOMPATIBLE SLEEVE FOR MESH INSERTION INSTRUMENT

(75) Inventors: Ferass Abuzaina, Shelton, CT (US); Ali Irfan, Shelton, CT (US); Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 51 days.

(21) Appl. No.: 13/451,962

(22) Filed: Apr. 20, 2012

(65) Prior Publication Data

US 2012/0259347 A1    Oct. 11, 2012

Related U.S. Application Data

(63) Continuation-in-part of application No. 12/891,962, filed on Sep. 28, 2010, which is a continuation-in-part of application No. 12/834,456, filed on Jul. 12, 2010, which is a continuation-in-part of application No. PCT/IL2009/000188, filed on Feb. 18, 2009.

(60) Provisional application No. 61/029,386, filed on Feb. 18, 2008, provisional application No. 61/302,186, filed on Feb. 8, 2010.

(51) Int. Cl.
A61B 17/00    (2006.01)

(52) U.S. Cl.
USPC .......................................... 606/151; 606/213

(58) Field of Classification Search
None
See application file for complete search history.

(56) References Cited

U.S. PATENT DOCUMENTS

| 5,383,477 A * | 1/1995 | DeMatteis ............ 128/898 |
| 8,097,008 B2 * | 1/2012 | Henderson ............ 606/151 |
| 2009/0281563 A1 | 11/2009 | Newell et al. |
| 2010/0069930 A1 | 3/2010 | Roslin et al. |
| 2011/0004221 A1 | 1/2011 | Euteneuer et al. |
| 2011/0040310 A1 | 2/2011 | Levin et al. |
| 2011/0040311 A1 | 2/2011 | Levin et al. |
| 2013/0018395 A1 * | 1/2013 | Friedlander et al. ........ 606/151 |

FOREIGN PATENT DOCUMENTS

| EP | 0557963 A1 | 9/1993 |
| WO | WO 2009/104182 A2 | 8/2009 |
| WO | WO 2011/021082 A1 | 2/2011 |
| WO | WO 2012/112565 | 8/2012 |

OTHER PUBLICATIONS

European Search Report for EP 11250797.5-2320 date of completion is Jun. 12, 2012 (9 pages).
Extended European Search Report corresponding to EP 13 16 4453.6, completed Jul. 29, 2013 and mailed Aug. 5, 2013; (7 pp).

* cited by examiner

Primary Examiner — Melanie Tyson
Assistant Examiner — Todd J Scherbel

(57) ABSTRACT

At least one aspect of this disclosure includes a system for closing an aperture in a biological tissue, the system comprising a handle, an elongate shaft connected to the handle, a deployment scaffold connected to the shaft, the deployment scaffold comprising a frame and a plurality of deployment arms hingedly connected to the frame, wherein the frame is configured to move from a retained position to at least one deployed position, a plurality of clips connected to the arms, wherein the clips are configured to releasably retain a surgical implant, and at least one sleeve selectively disposed at least partially over at least one of the plurality of arms when the frame is in the retained position, and selectively exposing at least one of the clips in the deployed position.

15 Claims, 16 Drawing Sheets

BIOCOMPATIBLE SLEEVE FOR MESH INSERTION INSTRUMENT

CROSS-REFERENCE TO RELATED APPLICATIONS

The present application is a is a continuation-in-part of U.S. patent application Ser. No. 12/891,962, filed on Sep. 28, 2010, which is a continuation-in-part of U.S. patent application Ser. No. 12/834,456, filed Jul. 12, 2010, which is a continuation-in-part of PCT international patent application number PCT/IL2009/000188, filed Feb. 18, 2009, which claims the benefit of and priority to U.S. provisional patent application Ser. No. 61/029,386, filed Feb. 18, 2008. The present application also claims the benefit of and priority to U.S. provisional patent application Ser. No. 61/302,186, filed Feb. 8, 2010. The contents of each of these prior applications are incorporated by reference herein in their entirety.

FIELD OF THE INVENTION

This invention generally relates to a device and method for reversibly coupling an implant to an implant deployment device.

BACKGROUND

An object of the present invention is to provide an apparatus and a method for performing corrective surgery on internal wounds such as a hernia where invasion of the patient's body tissues is minimized and resultant trauma is reduced.

A hernia is a protrusion of a tissue, structure, or part of an organ through the muscular tissue or the membrane by which it is normally contained. In other words, a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery, patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques, several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the implant and then to attach the implant to the tissue.

There are many patents and patent applications relating to attaching a prosthesis implant to a tissue via tacks. Each patent and patent application describes a different attachment mechanism via different anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body.

Most tissue anchors secure the tissue by impaling it with one or more posts or legs that are bent or crimped to lock the tissue into position. Thus, most traditional anchors are rigid or are inflexibly attached to the tissue. For example PCT No. WO 07/021,834 describes an anchor having two curved legs that cross in a single turning direction to form a loop. Those two curved legs are adapted to penetrate tissue in a curved pathway. U.S. Pat. No. 4,485,816 describes surgical staple made of shape memory alloy. The staple is placed in contact of the tissue and then heated. The heating causes the staple to change its shape thus, penetrating the tissue.

U.S. Pat. No. 6,893,452 describes a tissue attachment device that facilitates wound healing by holding soft tissue together under improved distribution of tension and with minimal disruption of the wound interface and its nutrient supplies.

U.S. Pat. No. 6,517,584 describes a hernia implant which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. No. 5,364,004; U.S. Pat. No. 5,662,662; U.S. Pat. No. 5,634,584; U.S. Pat. No. 5,560,224; U.S. Pat. No. 5,588,581; and in U.S. Pat. No. 5,626,587.

There are a few patent and patent applications teaching the deployment of implants. For example U.S. Pat. No. 5,836,961 which relates to an apparatus used for developing an anatomic space for laparoscopic hernia repair and an implant for use therewith. The apparatus of U.S. Pat. No. 5,836,961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More patent literature can be found in PCT No. WO 08/065,653 which relates to a device especially adapted to deploy an implant within a body cavity. The device is an elongate open-bored applicator and comprises (a) at least one inflatable contour-balloon, (b) at least one inflatable dissection balloon. The inflatable contour-balloon and the inflatable dissection balloon are adjustable and located at the distal portion. The elongate open-bored applicator additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

Although all the above described patents and patent applications demonstrate attachment means or deployment means, none of the literature found relates to a reversible connection device which enable a reversible coupling between the implant and the implant deployment device.

Thus, there is still a long felt need for a device that will enable a reversible connection between the implant and the implant deployment device.

SUMMARY

It is one object of the present invention to provide an active reversible connection mechanism adapted to provide a reversible attachment between a prosthetic implant and an implant deployment device, wherein said attachment can be actively reversed without requiring any application of force on said implant.

It is another object of the present invention to provide the active reversible connection mechanism as defined above, wherein said active reversible connection mechanism comprising at least one clip, hinge-like coupled to said implant deployment device, adapted to attach said implant to said implant deployment device: Said clip is characterized by having at least three configurations: (i) a horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate; such that (i) when said clip is in said horizontal configuration said attachment between said implant and said implant deployment device is obtained; (ii) when said clip is in said free motion configuration said detachment between said implant and said implant deployment device is obtained.

It is another object of the present invention to provide the active reversible connection mechanism as defined above, additionally comprising at least one locking bar characterized by at least two configurations: (i) lock configuration in which said lock bar maintains said clip in said horizontal configuration; and, (ii) free configuration in which said locking bar enables said clip a free movement.

It is another object of the present invention to provide the active reversible connection mechanism as defined above, wherein said active reversible connection additionally comprising at least one detachment actuator adapted to reversibly transform said locking bar from said lock configuration to said free configuration.

It is another object of the present invention to provide the active reversible connection mechanism as defined above, wherein said attachment between said implant and said implant deployment device is obtained once said locking bar is in its said lock configuration and said at least one clip is in said horizontal configuration such that the same at least partially penetrates said implant.

It is another object of the present invention to provide the active reversible connection mechanism as defined above, wherein said detachment is achieved by transforming said locking bar from said lock configuration to said free configuration via said at least one detachment actuator.

It is another object of the present invention to provide the active reversible connection mechanism as defined above, wherein said detachment actuator comprises a wire; further wherein said wire is attached to said lock bar.

It is another object of the present invention to provide the active reversible connection mechanism as defined above, wherein said transformation of said clip from said vertical configuration into their said horizontal configuration is performed manually by the physician or by the aid of a dedicated device.

It is another object of the present invention to provide a method for attaching a prosthetic implant to an implant deployment device. The method comprising steps selected inter alia from:

a. obtaining an active reversible connection mechanism adapted to provide a reversible attachment between said prosthetic implant and said implant deployment device; wherein said attachment can be actively revered without requiring any application of force on said implant; said active reversible connection comprising
 i. at least one clip, hinge-like coupled to said implant deployment device, adapted to attach said implant to said implant deployment device: Said clip is characterized by having at least three configurations: (i) horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate;
 ii. at least one locking bar characterized by at least two configurations: (i) lock configuration in which said lock bar maintains said clip in said horizontal configuration; and, (ii) free configuration in which said locking bar enables said clip a free movement; and,
b. providing said clips in said vertical configuration;
c. providing said locking bar in said lock configuration;
d. threading said implant through said clip;
e. transforming said clip into its said horizontal configuration thereby providing said attachment between said implant and said implant deployment device;

It is another object of the present invention to provide the method as defined above, additionally comprising step of providing said active reversible connection with at least one detachment actuator.

It is another object of the present invention to provide the method as defined above, additionally comprising step of reversibly transforming said locking bar from said lock configuration to said free configuration via said detachment actuator; thereby enabling free rotation of said clip such that detachment between said implant and said implant deployment device is obtained.

It is another object of the present invention to provide the method as defined above, additionally comprising step of introducing said implant deployment device into a body cavity.

It is another object of the present invention to provide the method as defined above, additionally comprising step detaching said implant from said implant deployment device.

It is another object of the present invention to provide the method as defined above, wherein said detachment additionally comprising steps of reversibly transforming said locking bar from said lock configuration to said free configuration via said detachment actuator; thereby enabling said clip to rotate freely such that said detachment between said implant and said implant deployment device is obtained.

It is another object of the present invention to provide a hernia kit useful in minimal invasive hernia surgery, comprising:
 a. a implant;
 b. implant deployment device, adapted to deploy said implant within the abdominal cavity; and,
 c. an active reversible connection mechanism for reversible attaching said implant to said implant deployment device;
 wherein attachment can be actively revered without requiring any application of force on said implant.

It is another object of the present invention to provide the hernia kit as defined above, wherein said active reversible connection mechanism comprising:
 a. at least one clip, hinge-like coupled to said implant deployment device, adapted to attach said implant to said implant deployment device: Said clip is characterized by having at least three configurations: (i) horizontal configuration in which said clip is substantially horizontal with respect to said implant deployment device; (ii) a vertical configuration in which said clip is substantially vertical with respect to said implant deployment device; and, (iii) a free motion configuration in which said clip is free to rotate; such that (i) when said clip is in said horizontal configuration said attachment between said implant and said implant deployment device is obtained; (ii) when said clip is in said free motion configuration said detachment between said implant and said implant deployment device is obtained.

It is another object of the present invention to provide the hernia kit as defined above, additionally comprising at least one locking bar characterized by at least two configurations: (i) lock configuration in which said lock bar maintains said clip in said horizontal configuration; and, (ii) free configuration in which said locking bar enables said clip a free movement.

It is another object of the present invention to provide the hernia kit as defined above, wherein said active reversible connection additionally comprising at least one detachment actuator adapted to reversibly transform said locking bar from said lock configuration to said free configuration.

It is another object of the present invention to provide the hernia kit as defined above, wherein said attachment between said implant and said implant deployment device is obtained once said locking bar is in its said lock configuration and said at least one clip is in said horizontal configuration such that the same at least partially penetrates said implant.

It is another object of the present invention to provide the hernia kit as defined above, wherein said detachment is achieved by transforming said locking bar from said lock configuration to said free configuration via said at least one detachment actuator.

It is still an object of the present invention to provide the hernia kit as defined above, wherein said detachment actuator comprises a wire; further wherein said wire is attached to said lock bar.

It is lastly an object of the present invention to provide the hernia kit as defined above, wherein said transformation of said clip from said vertical configuration into their said horizontal configuration is performed manually by the physician or by the aid of a dedicated device.

At least one aspect of this disclosure includes a system for closing an aperture in a biological tissue, the system including a handle, an elongate shaft connected to the handle, a deployment scaffold connected to the shaft, the deployment scaffold having a frame and a plurality of deployment arms hingedly connected to the frame, wherein the frame is configured to move from a retained position to at least one deployed position, a plurality of clips connected to the arms, wherein the clips are configured to releasably retain a surgical implant, and at least one sleeve selectively exposing at least one of the clips in a first position, and selectively disposed at least partially over at least one of the plurality of arms in a second position; at least one sleeve selectively disposed at least partially over at least one of the plurality of arms when the frame is in the retained position, and selectively exposing at least one of the clips in the deployed position.

In at least one aspect of this disclosure, the at least one sleeve selectively covers at least one hinge connecting the arms to the frame in the second position.

In at least one aspect of this disclosure, the at least one sleeve covers a plurality of clips in the second position.

In at least one aspect of this disclosure, the system further includes at least one sleeve for each of the plurality of arms.

In at least one aspect of this disclosure, the sleeve is made of a rigid material or semi-rigid material.

In at least one aspect of this disclosure, the rigid or semi-rigid material has at least one material selected from the group consisting of a metal or a plastic.

In at least one aspect of this disclosure, the sleeve is a flexible material.

In at least one aspect of this disclosure, the flexible material includes at least one of a fabric, a plastic, or rubber.

In at least one aspect of this disclosure, the sleeve is a bio-compatible material.

In at least one aspect of this disclosure, the system further includes at least one sleeve positioning member attached to the at least one sleeve, the member configured to allow the sleeve to expose at least one of the clips in the first position and to position the at least one sleeve over at least a portion of at least one of the plurality of arms in the second position.

In at least one aspect of this disclosure, the frame is assembled such that at least one proximal member attaches to the elongate shaft at a first hinge and to at least one of the arms at a second connection, wherein the at least one of the arms is further connected to at least one distal member at a third hinge, and the at least one distal member is connected to a actuation member at a fourth hinge.

In at least one aspect of this disclosure, the at least one sleeve is disposed over the at least one distal member when the frame is in the deployed position, and disposed over at least one of the arms when the frame is in the retracted position. In at least one aspect of this disclosure, the system further includes a means for selectively disposing the at least one sleeve over the at least one distal member and at least one of the arms.

In at least one aspect of this disclosure, a method for protecting tissue during a laparoscopic procedure is disclosed, including providing a system for closing an aperture in a biological tissue including a handle, an elongate shaft connected to the handle, a deployment scaffold connected to the shaft, the deployment scaffold including a frame and a plurality of deployment arms hingedly connected to the frame, wherein the frame is configured to move from a retained position to at least one deployed position, a plurality of clips connected to the arms, wherein the clips are configured to releasably retain a surgical implant, and at least one sleeve selectively exposing at least one of the clips in a first position, and selectively disposed at least partially over at least one of the plurality of arms in a second position; transitioning the frame from the deployed position to the retained position, and causing the at least one sleeve to be moved to the second position.

In at least one aspect of this disclosure, the method, further includes inserting the system into a surgical site when the frame is in the retained position.

In at least one aspect of this disclosure, the method further includes attaching a implant to the clips before inserting the system into the surgical site and expanding the frame from the retained position to the deployed position after inserting the system into the surgical site.

In at least one aspect of this disclosure, the method, further includes placing the arms on a desired location inside the surgical site and deploying an implant from the system to the desired location when the frame is in the deployed position.

In at least one aspect of this disclosure, the transitioning step further comprises retracting the frame to the retained position from the deployed position after deploying the implant, moving the at least one sleeve into the second position after deployment of the implant, and removing the system from the surgical site after moving the at least one sleeve into the second position.

In at least one aspect of this disclosure, the method, further includes removing the system from the surgical site after causing the at least one sleeve to be moved into the second position when the frame is in the retained position.

BRIEF DESCRIPTION OF THE DRAWINGS

The invention is herein described, by way of example only, with reference to the accompanying drawings, wherein.

DETAIL DESCRIPTION OF THE SPECIFIC EMBODIMENTS

Figure 1A:
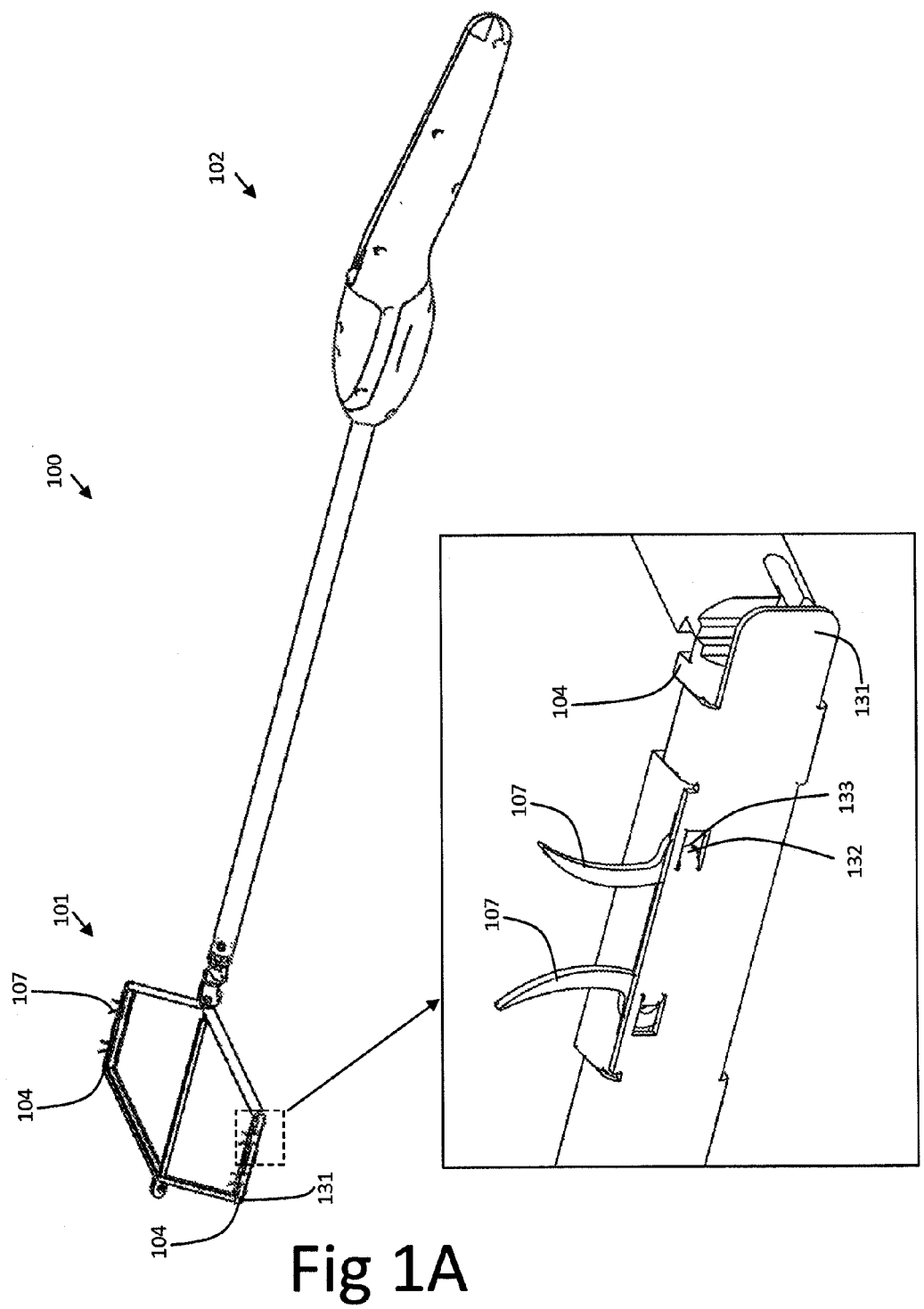
FIG. 1A illustrates an example of a implant deployment device which comprises said active reversible connection mechanism.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides means and method for creating a reversible and active connection between a implant and a implant deployment device.

The present invention provides an active reversible connection mechanism between a prosthetic implant and an implant deployment device wherein said connection can be performed during a surgery at a standard surgery room by the medical staff.

Furthermore, the present invention provides means so as to enable the surgeon to actively eliminate said attachment once detachment between said implant deployment device and said implant is necessary.

It should be emphasized that some of the major advantages of the present invention, with respect to the prior art, is to provide a fast and intuitive method for creating a reliable connection between an implant and an implant deployment device in the surgery room. Embodiments of an implant include, but are not limited to, a surgical patch, a surgical mesh, or other biocompatible implants usable in repairing a defect in body tissue.

In addition, the present invention provides means to actively disconnect said implant from said implant deployment device, when said disconnection is desired without the need to exert large forces on said implant and/or said tissue.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components.

The term "hinge like connection" can refer to a standard hinge or to a living hinge (i.e., a thin flexible hinge (flexure bearing) made from plastic that joins two rigid parts together while allowing them to bend along the line of the hinge).

The term "controlled deployment" refers hereinafter to an implant deployment which is continuous; i.e., the deployment is not binary but analogous—there are several deployment levels. This is in contrast so conventional deployment system is now days (see for example U.S. Pat. No. 5,370,650), in which the deployment of the implant relies upon the elasticity of a loop member surrounding the implant such that the implant can be either fully folded or fully unfolded. No intermediate are enabled. In the present invention, there can be several deployment stages.

The term "bidirectional" or "fully reversible deployment" refers hereinafter to the deployment of the implant, which according to the present invention, is fully reversible. In other words, the implant deployment is bidirectional, i.e., the implant can be fully folded (i.e., deployed within the body) and then, if the surgeon desires, the implant can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh within the abdominal cavity so as to fit to the hernia. Usually the mesh is not symmetric in shape (i.e., rectangular or i.e., ellipse)—therefore it has different directions. By rotating the mesh within the abdominal cavity—one can decide which direction is turned where.

The term "adjusting" refers hereinafter to rolling, folding, and winding of the implant, thus preparing and enabling the insertion of said implant into the abdominal cavity.

The term "active reversible connection" refers hereinafter to a coupling between the implant and the implant deployment device implant deployment device in which the coupling/decoupling between the implant and the implant deployment device is enabled by an act performed by the user (namely the physician). Once said User performed said act, said coupling/decoupling is canceled.

According to the present invention the coupling/decoupling is obtained actively via the aid of dedicated clips which are characterized by at least two configurations:
 (a) substantially horizontal/parallel configuration (in which an attachment between the implant and the implant deployment device is provided);
 (b) substantially vertical configuration; and,
 (c) a configuration in which the clips are free to rotate.

Before explaining the figures, it should be understood that the invention is not limited in its application to the details of construction and the arrangement of the components set forth in the following description or illustrated in the drawings. The invention can be carried out in various ways.

Reference is now being made to FIG. 1A illustrates an example of an implant deployment device 100 which comprises said active reversible connection mechanism.

implant deployment device 100 is defined hereinafter as a surgical device which can introduce a implant into a body cavity of a patient; implant deployment device 100 can deploy said implant such that it is at least partially spared inside the body cavity; alternatively implant deployment device 100 can only introduce said implant into the body cavity without performing any deployment.

In general, implant deployment device 100 comprises at least two portions: a distal portion 101 and a proximal portion 102. The proximal portion is adapted to remain outside the body, adjacently to the user and the distal portion 101 is adapted to be inserted into the body.

The distal portion comprises at least one frame arm 104 to which the implant is attached. Each frame arm 104 comprises said active reversible connection mechanism which provides reversible attachment between each frame arm 104 and the implant 106 such that said implant can be rolled/folded on said distal portion 101, and inserted into the patient's body cavity through a laparoscopic cannula or a small incision.

It should be noted that the term reversible refers hereinafter to the ability to both attach the implant to the implant deployment device and to decouple the same from the implant deployment device.

Said active reversible connection mechanism comprises at least one clip 107. Said clip is coupled to said frame arm 104 by hinge tab 132. Said active reversible connection is covered by cover 131 which is attached to the frame arm 104. Cover 131 comprises at least one hinge tab 132 which is adapted to hold said clip 107 attached to frame arm 104 an to serve as a hinge allowing free rotation of said clip 107. Said hinge tab 132 is inserted through hinge hole 133, located at clip 107 and through hole 134, located at frame arm 104.

Reference is now being made to FIGS. 2A-2D which illustrate the internal operation of said active reversible connection mechanism. For the purpose of illustration only, cover 131 is removed from these drawings.

A locking bar 203 is located inside groove 204 at frame arm 104. Said locking bar 203 can move linearly inside said groove 204 and comprises at least one groove 205. Said locking bar 203 is characterized by at least two positions: free position, in which each of said groove/s 205 is substantially located below said clip 107 (see FIGS. 2C and 2D), and lock position, in which said groove 205 is located away from said clip 107 (see FIGS. 2A and 2B).

In the lock position of the locking bar 203, the clip 107 are substantially perpendicular to the frame arm 104; and in free position of the locking bar 203, the clip 107 are free to rotate (hence, as will be discussed hereinafter a detachment is enabled).

A disconnection wire 206 is attached to said locking bar 203. Said wire 206 can be pulled proximally to the proximal portion 102 and is adapted to transform said locking bar 203 from its said lock position into its said free position.

According to this embodiment, each clip 107 comprises at least 3 sections: protruding portion (PP) 201 adapted to protrude through said implant during said connection process, hinge hole 133, and locking tab 202 which is tilted toward frame arm 104.

Figure 2A:
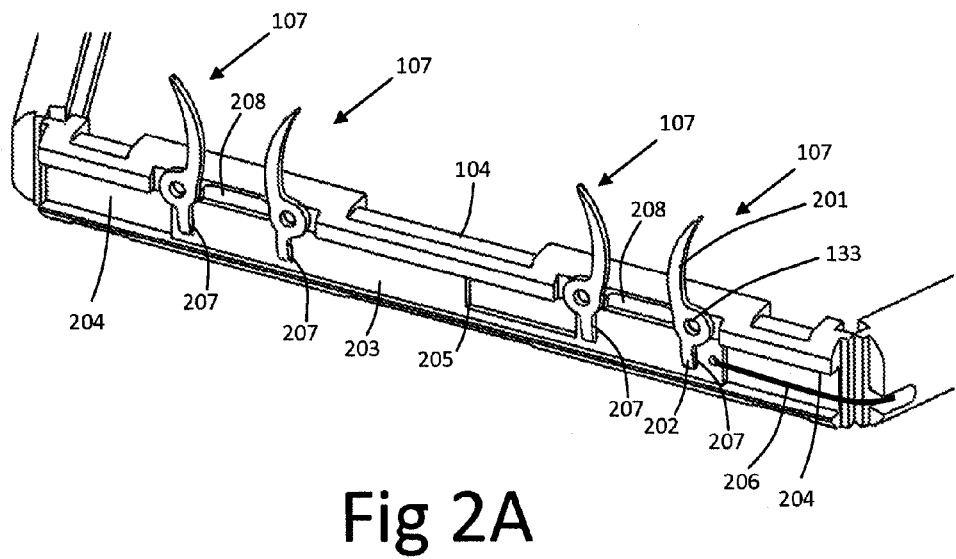
FIGS. 2A-2D illustrate the internal operation of said active reversible connection mechanism.
Figure 2B:
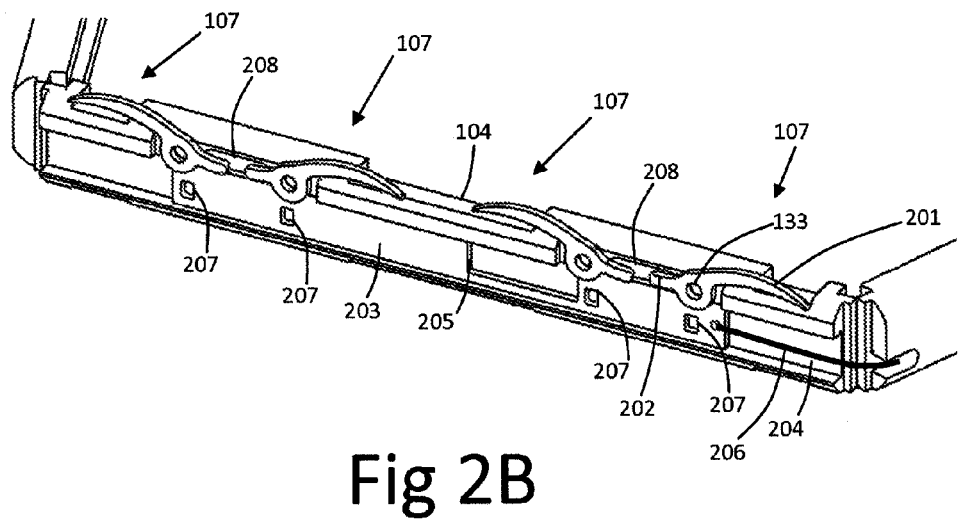
Figure 2C:
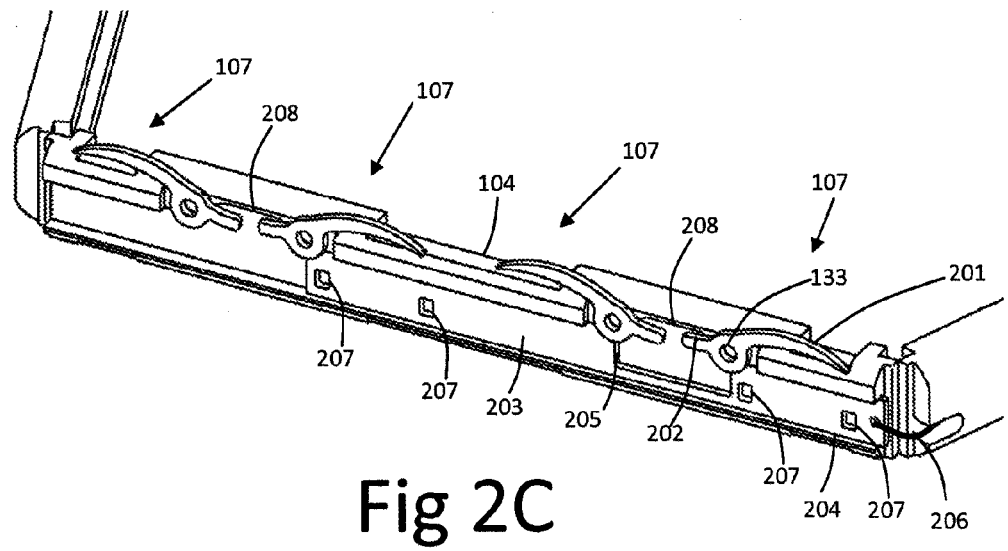
Figure 2D:
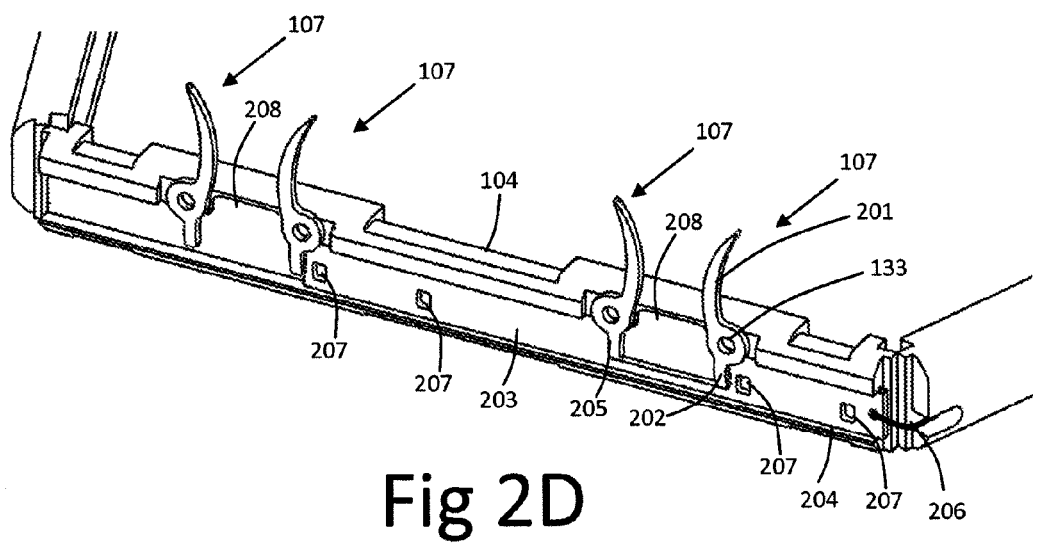

Each of said clip 107 is characterized by at least two configurations: horizontal/parallel configuration in which said clip 107 is substantially horizontal and parallel to said frame arm 104 (FIGS. 2B, 2C) and vertical configuration in which said clip 107 is substantially vertical with respect to said frame arm 104 (FIGS. 2A and 2D).

At least one holding hole 207 is located at said locking bar 203 and is adapted to hold said clip 107 in its vertical configuration.

At least one niche 208 in located at frame arm 104 adapted to accommodate said locking tab 202 of said clip 107 while the last is in its said horizontal/parallel configuration.

Reference is now being made to FIGS. 3A-3D illustrating a method of using said active reversible connection mechanism in order to provide said reversible connection between said implant and said implant deployment device 100. Again, for the purpose of illustration only, cover 131 was removed from these drawings.

Figure 3A:
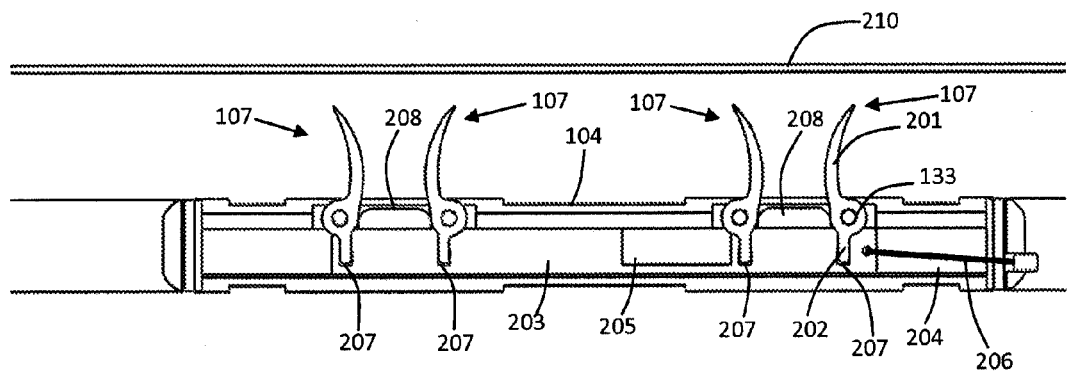
FIGS. 3A-3E illustrate a method of using said active reversible connection mechanism for providing said reversible connection between said implant and said implant deployment device.

FIG. 3A illustrates the initial state of said active reversible connection mechanism in which all of said clip 107 are in their vertical configuration and said locking bar 203 is positioned in said lock position.

Figure 3B:
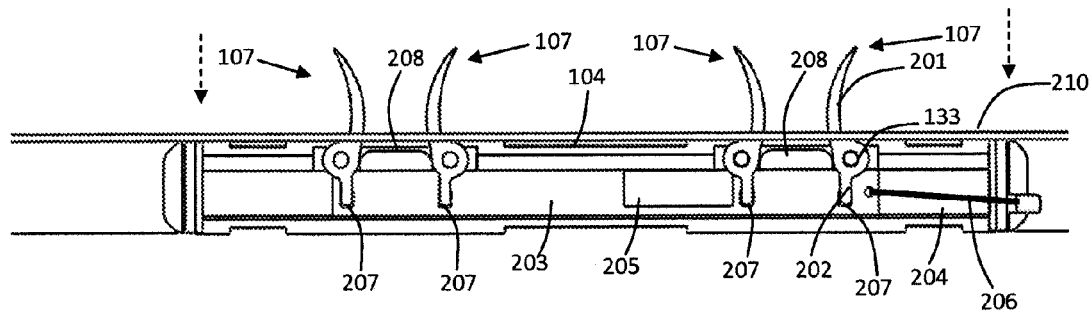

As can be seen in the figure, said locking tab 202 of each said clip 107 is located inside said holding hole 207, therefore each clip 107 is held in its said vertical configuration and can penetrate a implant 210 whilst the last is mounted on top of said implant deployment device (see FIG. 3B).

Figure 3C:
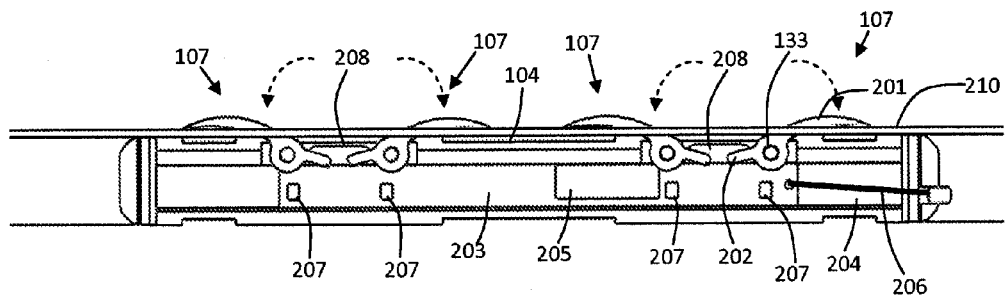

Once said implant is mounted, each of said clip 107 is transformed from said vertical configuration into their said horizontal configuration (see FIG. 3C).

Said transformation can be achieved either manually (i.e., the physician will manually rotate the clips 107 thereby transforming them from said vertical configuration into their said horizontal configuration) or by the aid of a dedicated device.

Once said clip 107 is transformed to its horizontal configuration while said locking bar is in its said lock position, said locking tab 202 is sprigged into niche 208. Since the locking tab 202 is titled inwardly, if said clip 107 is pulled upwardly in this state, the locking tab 202 is stooped by the upper edge of said locking bar 203, therefore, the rotation back to said vertical configuration of said clip 107 is limited by said locking bar 203 and said clips 107 are locked in said horizontal configuration, holding said implant attached to said frame arm 104.

It should be pointed out that it is a unidirectional mechanism. In other words, if one tries to force clips 107 to its vertical configuration, locking tabs 202 will bump into locking bar 203.

Figure 3D:
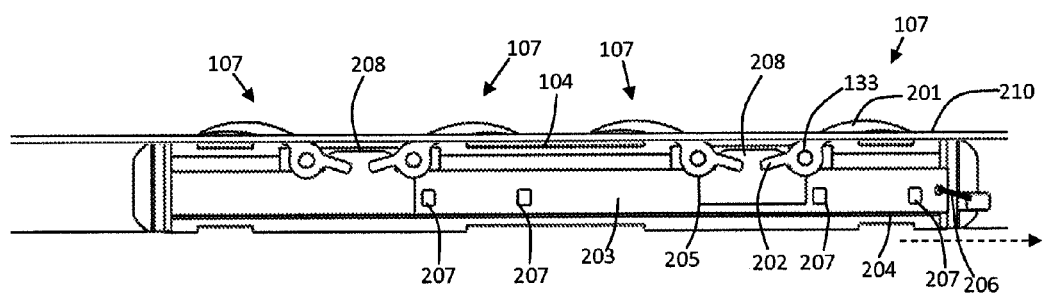
Figure 3E:
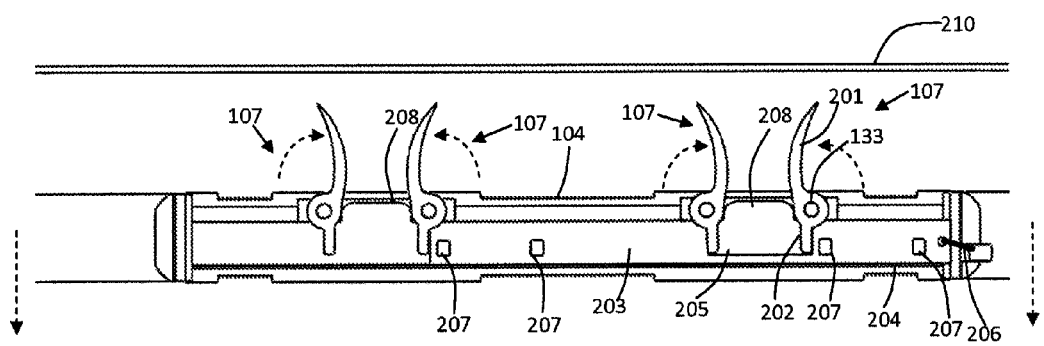

By further pulling said locking bar 203 towards the proximal portion the clips 107 are unlocked and can be rotated be back to its vertical configuration (see FIGS. 3D and 3E).

Once detachment between said implant 210 and said implant deployment device in desired, locking bar 203 is pulled backward by wire 206, changing the position of said locking bar form its said lock position into its said free position (see FIG. 3D). In said free position of the locking bar 203, the clips 107 are free to rotate (hence, as will be discussed hereinafter, a detachment between the implant deployment device and the implant is enabled).

Once locking bar 203 is positioned in said free position, said groove's 205 is located below said clips 107, therefore said locking bar 202 is no longer limiting the movement of said clips 107 enabling their free movement. In this state, detachment can be obtained by simply pulling said frame arm 104 away from said implant; as a result, said clips 107 rotate back into their said vertical configuration and are released from said implant (see FIG. 2E).

Reference is now made to FIG. 4A-4H, which illustrate an embodiment of a stapling apparatus 400 adapted for providing said reversible connection by said active reversible connection mechanism. Said stapling apparatus 400 comprises a frame 401 which holds the distal portion 101 of an implant deployment device 100. Four staplers 403 are connected to the frame 401 at each cornet by four separate hinges (either standard or living hinges). Each said stapler 403 is adapted to push down the implant 210 through a pair of clip 107 and to transform said clips 107 from a vertical position into a horizontal position (thus providing said reversible connection). Stapling presses 404 are located at the end of each stapler inside groove 405 and adapted to push clip 107 into horizontal position. Each pair of staplers 403 is connected via bridge 407 in order to prevent lateral movement of said staplers 403 during the stapling process. A snap groove 406 is located at the center of the frame 401 and adapted to reversibly hold said implant deployment device 100 attached to stapling apparatus 400 until said reversible attachment is obtained.

Figure 4A:
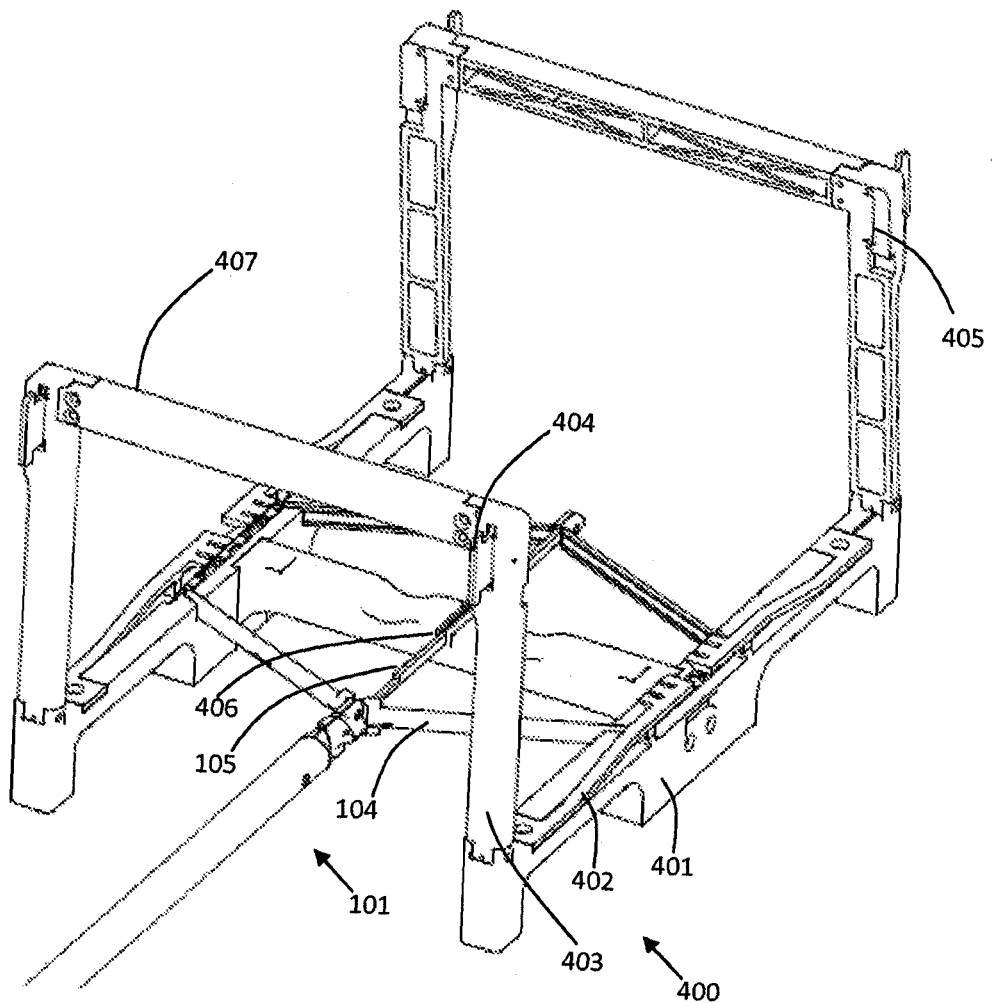
FIG. 4A-4H illustrate an embodiment of a stapling apparatus adapted for providing a reversible connection by the active reversible connection mechanism.
Figure 4B:
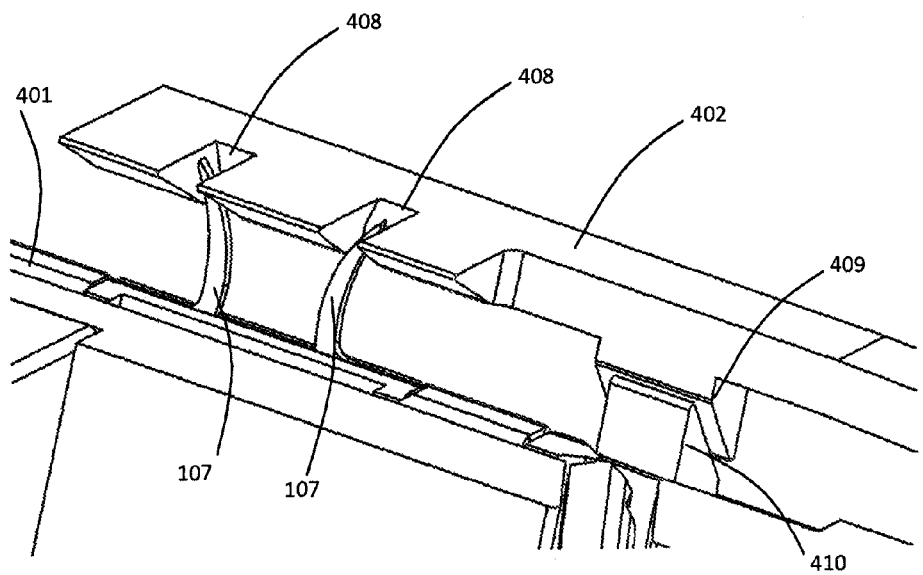
Figure 4C:
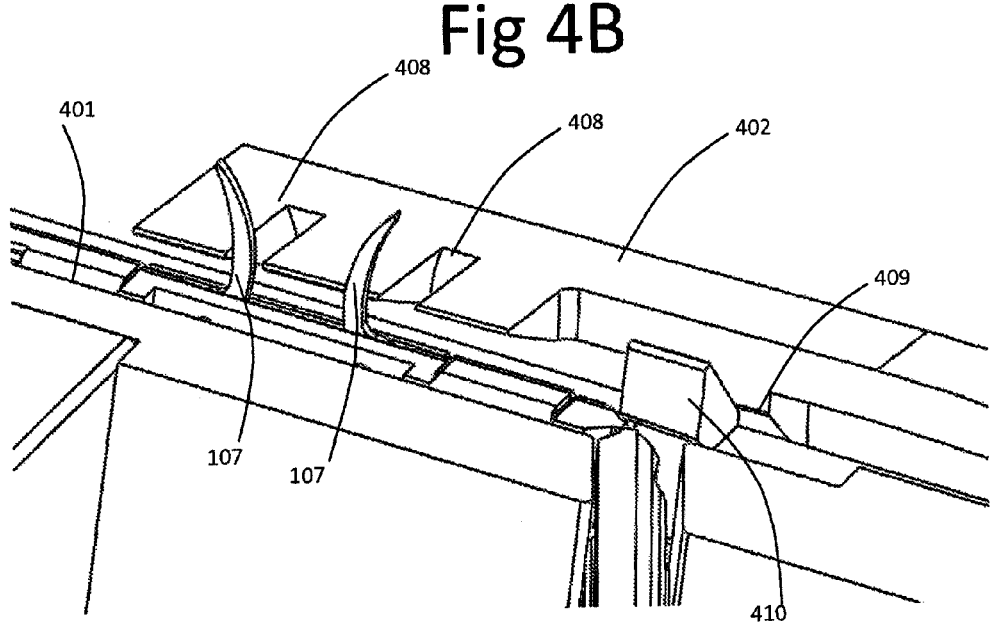
Figure 4D:
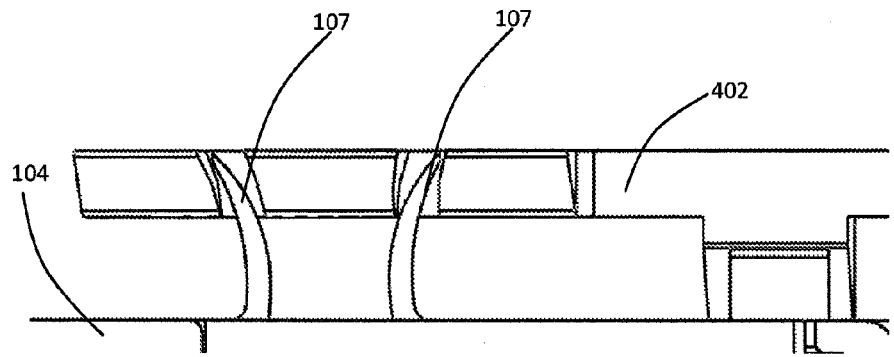
Figure 4E:
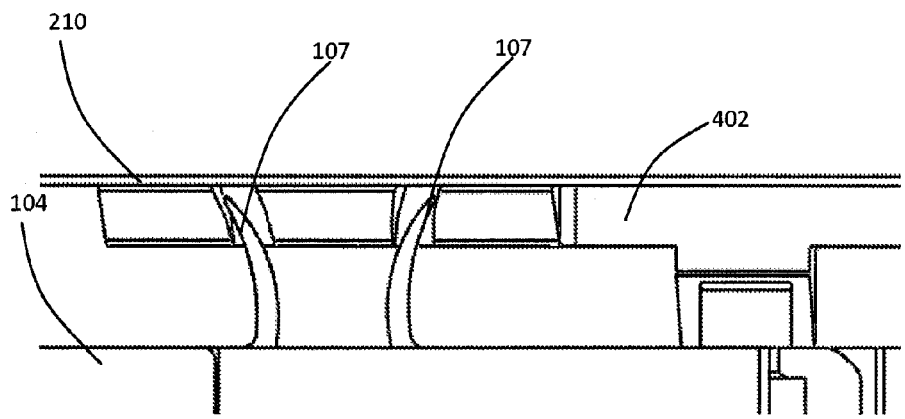

Each pair of clip 107 is held in a vertical position by clip holder 402. Each said clip holder 402 is adapted to hold a pair of clip 107 in vertical position in order to allow its insertion through the implant 210 during the stapling process. In addition, clip holder 402 is adapted the hold the clips vertical during shipment in order to allow stapling in the operation room without the need of any preparation. As illustrated in FIGS. 4B-4C, each clip holder 402 comprises two grooves 408 which hold the clip 107 in a vertical position. Once stapling process is preformed and the surgeon is lowering the stapler 403 toward the implant, each clip holder 402 is pushed down and as a result it is also moving laterally. In this state, since the clip 107 are extracted from groves 408, their transformation from vertical into horizontal position is enabled; said lateral movement of said clip holder 402 is obtained as bulge 409 at clip holder 402 is sliding along bulge 410 at the stapling frame 401 during the down movement of clip holder 402.

Figure 4F:
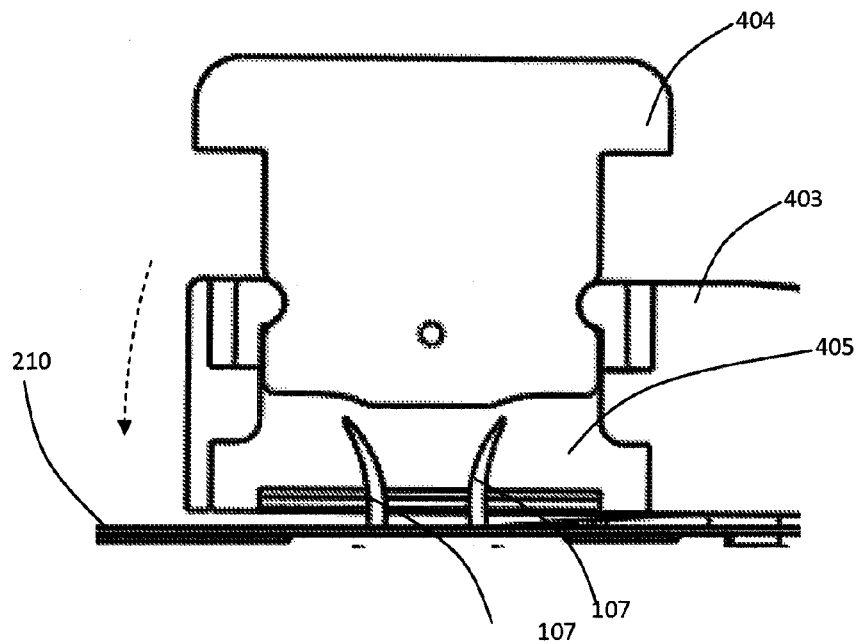
Figure 4G:
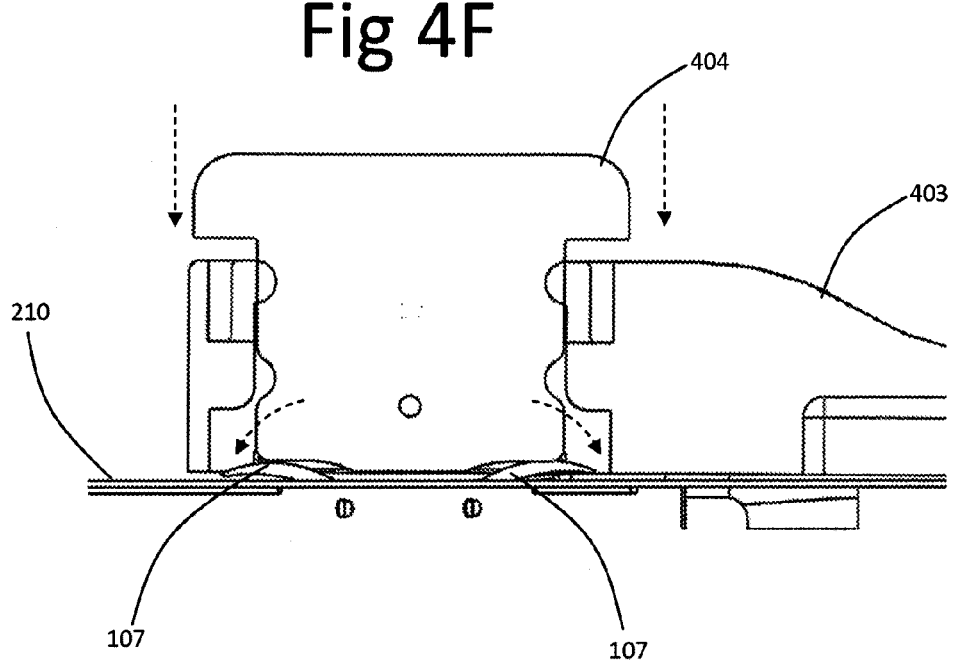

FIGS. 4D-4G illustrate the process of connecting the implant 210 to one pair of clip. At the initial stage (FIG. 4 D), the clips are held vertically by clip holder 402. Next, an implant 210 is places on top of the stapling apparatus (FIG. 4E); the stapler 403 is then lowered toward the implant 210 by the surgeon (or other member of the medical staff); as a result the two clip 107 are penetrating through implant 210 and into groove 405 (FIG. 4F). During the initial penetration, clip 107 is held by clip holder 402, thus premature transformation from vertical into horizontal position is prevented. Once the clip 107 are completely inserted into said implant 210, clip holder 402 is positioned laterally relative to the clip 107 (as also described is FIGS. 4B-4C); at this stage the surgeon push on stapler press 404 and lower it toward clip 107 (FIG. 4G), as a result clip 107 position is transformed form vertical position into horizontal position. Since the said lock bar 203 is located at its said lock position, once clip 107 are substantially horizontal position, they are locked in this stage, thus providing said reversible connection between implant 210 and implant deployment device 100. Once said connection is obtain with all clip 107, implant deployment device is removed from SA 400.

Figure 4H:
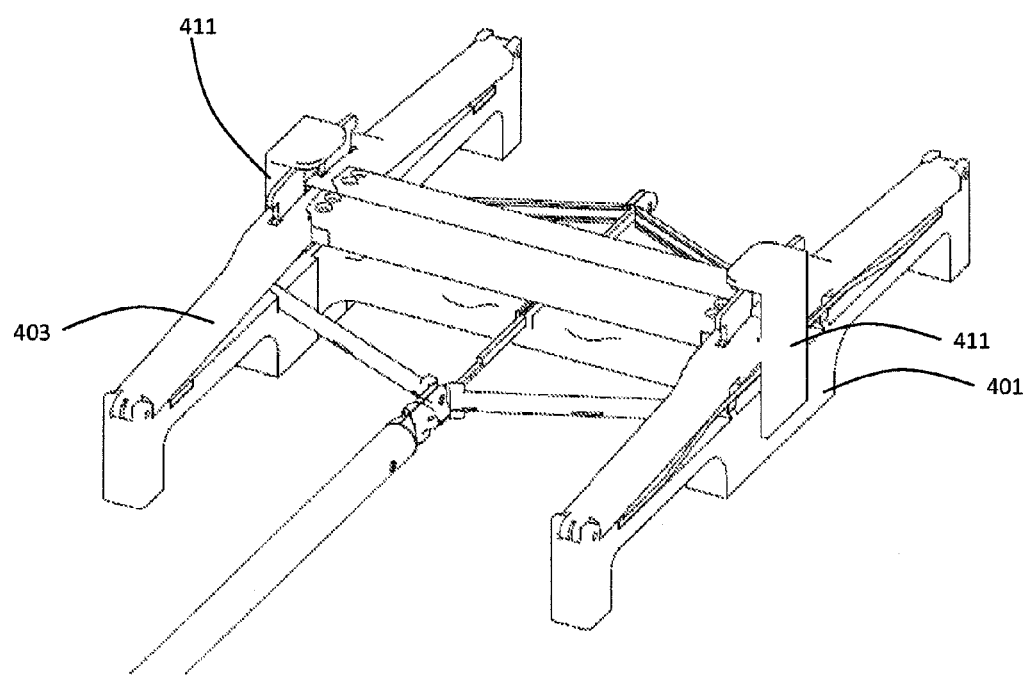

FIG. 4H illustrates the configuration of stapling apparatus 400 during shipment. In order to reduce package volume during shipment and to keep the device ready for stapling, at least one, preferably two, packaging caps 411 are utilized. Said caps 411 are reversibly attached to the frame 401, and adapted to retain stapler 403 in a substantially horizontal position during device shipment. In addition, said caps 411 also prevent down movement of stapler press 404, prevent lateral movement of clip holder 402 and prevent non-deliberate extraction of implant deployment device 100 from frame 401.

Once the device in removed from its packaging during the surgery, said pack caps 411 are removed by the medical staff in order to allow stapling of the implant 210 to the implant deployment device 100. Once the caps 411 are removed, the staplers 403 springs into horizontal position allowing the placement of implant 210 onto the stapling apparatus 400 and implant deployment device 100.

In order to allow tight spreading of the implant 210 during surgery, said stapling process is preformed while implant deployment device 100 is not completely opened; as a result, once implant deployment device is completely opened inside the abdominal cavity, it is stretched beyond its original dimension (as was during stapling) therefore tight spreading is obtained.

Figure 5:
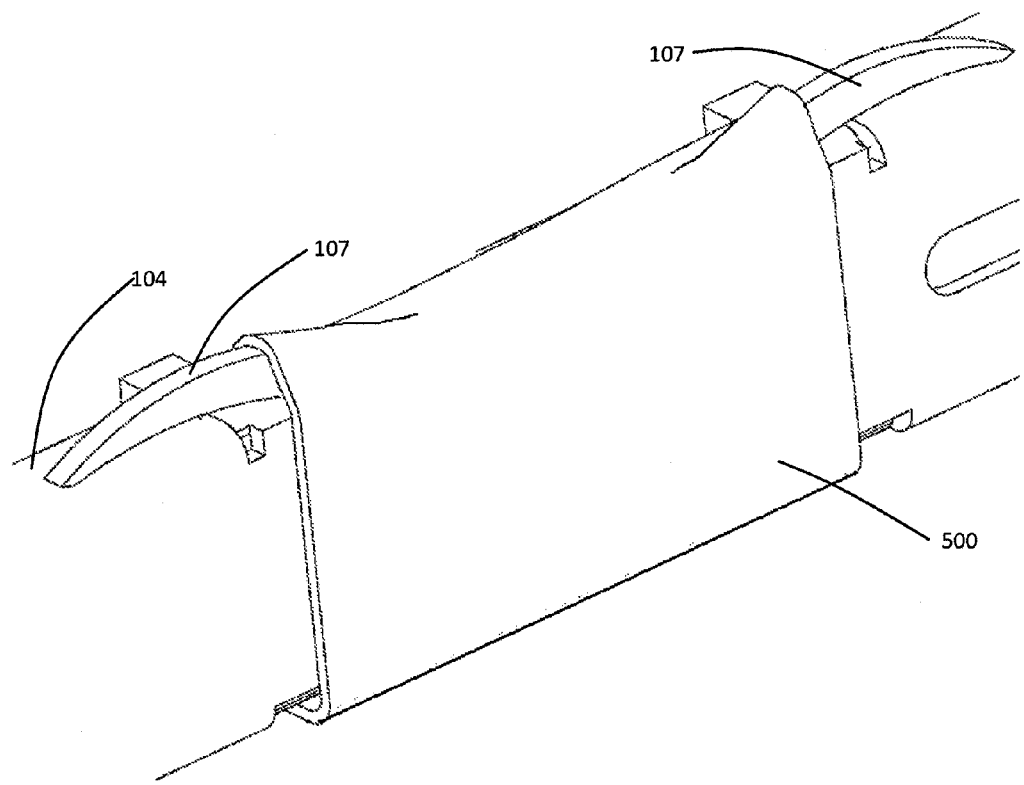
FIG. 5 illustrates an embodiment of a staple return spring.

Reference is now being made to FIG. 5 which illustrates an embodiment of a staple return spring 500. In general, staple return spring 500 is needed in order to return clip 107 into horizontal position immediate after detachment from the implant 210; this is necessary in order prevent damage to internal organs by the sharp tip of clip 107 and in order to prevent clip 107 from being caught at the trocar or at the tissue during device extraction.

Referring to FIG. 6A-6D, another embodiment of a system 600 for closing an aperture in a biological tissue is shown in different positions. The system 600 includes a handle 602 with an elongate shaft 601 connected to the handle 602.

Figure 6B:
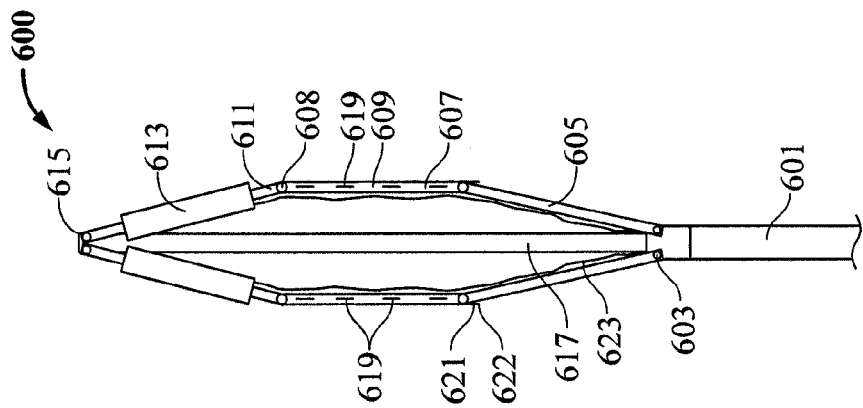
FIG. 6B illustrates an embodiment of a system for closing an aperture in a biological tissue having the frame in a retained position and with the sleeve in a first position.
Figure 6A:
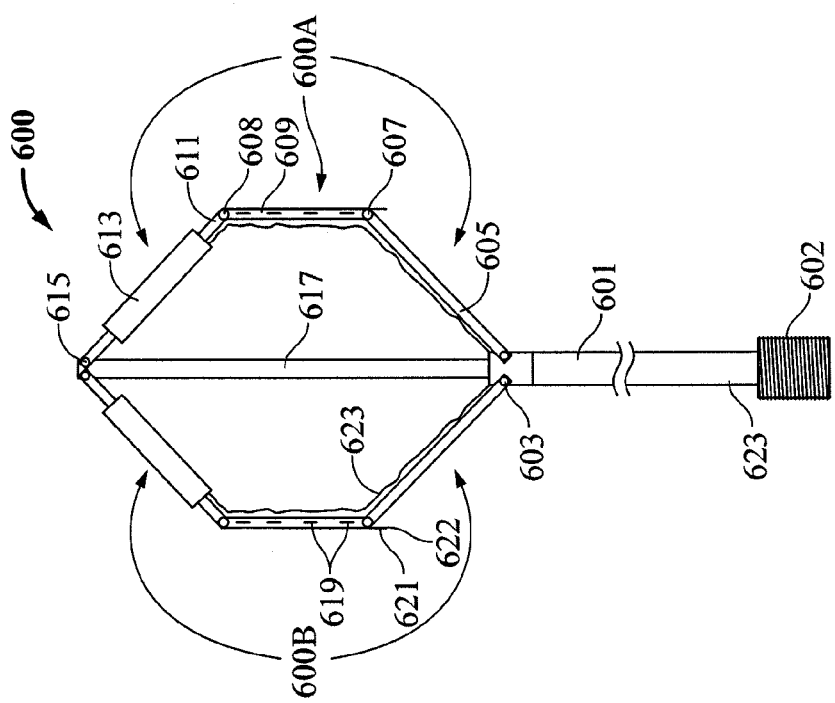
FIG. 6A illustrates an embodiment of a system for closing an aperture in a biological tissue having a frame in a deployed position and with a sleeve in a first position.
Figure 6D:
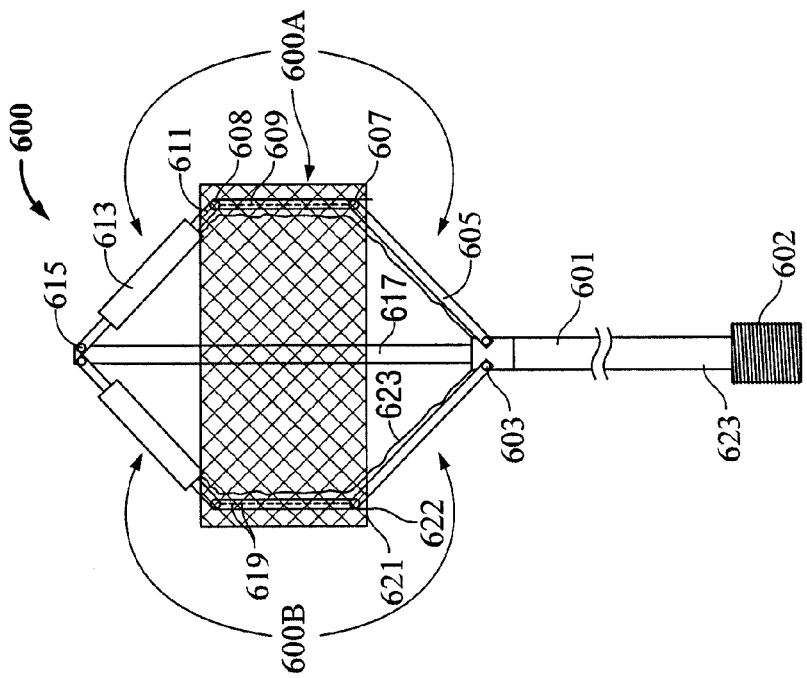
FIG. 6D illustrates an embodiment of a system for closing an aperture in a biological tissue having a frame in a deployed position with a pad attached thereto and with the sleeve in a first position.
Figure 6C:
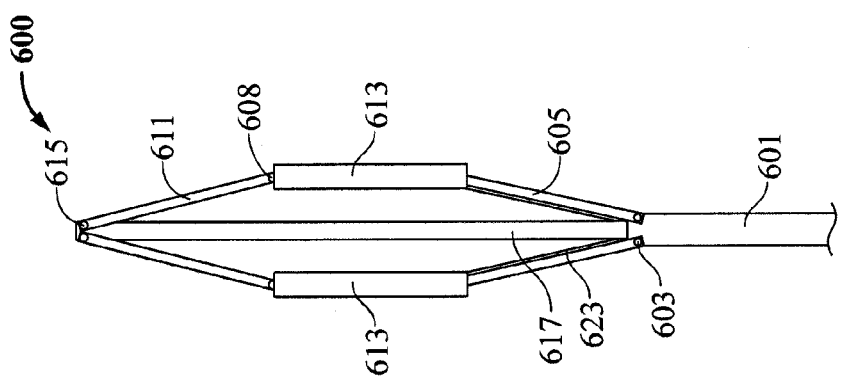
FIG. 6C illustrates an embodiment of a system for closing an aperture in a biological tissue having the frame in a retained position and with the sleeve in a second position.

A deployment scaffold 600A is connected to the shaft 601, the deployment scaffold 600A having a frame 600B and a plurality of deployment arms 609 hingedly connected to the frame 600B. The deployment arms 609 may be substantially similar to the active reversible connection mechanism as described above. The frame 600B may be any arrangement of members holding the deployment arms 609 in a desired position. As shown in FIG. 6A-6C, the frame 600B may include at least one proximal member 605, at least one distal member 611, and at least one actuation member 617. The frame 600B may be assembled such that the at least one proximal member 605 attaches to the elongate shaft 601 at a first hinge 603 and to at least one of the deployment arms 609 at a second connection 607. The frame 600B may further be assembled such that the at least one of the deployment arms 609 may further be connected to the at least one distal member 611 at a third connection 608, and the at least one distal member 611 may be connected to the actuation member 617 at a fourth connection 615. Thus, the deployment scaffold 600A may include members 605, 609, 611, and 617, and connections 603, 607, 608 and 615. Connections 603, 607, 608 and 615 may be any type of hinge, such as but not limited to, mechanical hinges, living hinges, ball and socket joints, etc. The frame 600B/scaffold 600A is configured to move from a retained position as shown in FIGS. 6B and 6C, to at least one deployed position as shown in FIG. 6A, and vice versa by distal and proximal movement of the actuation member 617, respectively.

A plurality of clips 619 are connected to the deployment arms 609, wherein the clips 619 are configured to releasably retain a surgical implant as described above.

In some embodiments, at least one sleeve 613 is disposed on the system 600. The at least one sleeve 613 may be made from a rigid material such as but not limited to a hard plastic or metal. In some embodiments, the at least one sleeve 613 includes a flexible material such as but not limited to a soft plastic, rubber, or fabric. The at least one sleeve 613 may include a bio-compatible material. The at least one sleeve 613 may loosely or tightly fit around the frame 600B members and/or the deployment arms 609 as desired.

The at least one sleeve 613 may be selectively positionable from a first position, whereby the clips 619 are uncovered as shown in FIG. 6A, to a second position at least partially over one or more of the plurality of deployment arms 609 to cover at least one clip 619. It should be noted that the position of the at least one sleeve 613 is not related to the positioning of the frame 600B, and the at least one sleeve 613 may cover or expose the clips 619 whether the frame 600B is in the deployed or retained position. The at least one sleeve 613 may be biased toward the clip exposing position as shown in FIGS. 6A and 6B by a biasing member such as, but not limited to, a spring. The system 600 may include at least one sleeve 613 for each of the plurality of arms 609.

The at least one sleeve 613 may be shaped to further selectively cover at least one of the hinges connecting the deployment arms 609 to the frame 600B when the frame 600B is in the either the retained position or deployed position. At least one of the hinges may have a hinge cover 621 having a proximal portion 622, and the at least one sleeve 613 may cover at least one hinge cover 621 and/or the proximal portion 622 thereof.

The at least one sleeve 613 may begin in the first position and be moved to the second position to cover the clips 619 and/or the hinge covers 621 and/or the proximal portion 622 thereof.

The system 600 may further include at least one sleeve deployment system. In some embodiments, the at least one sleeve deployment system includes at least one sleeve positioning member 623 attached to the at least one sleeve 613, the member 623 configured to position the at least one sleeve 613 over at least a portion of at least one of the plurality of arms 609 when the frame 600B is in the retracted or collapsed position, and to allow the sleeve 613 to expose at least one of the clips 619 in the deployed or expanded position. The sleeve positioning member 623 is adapted for translating the sleeve 613 proximally and distally. The sleeve positioning member 623 may include, for example, at least one cable, pushrod or other device for actuating the sleeve 613.

Figure 7:
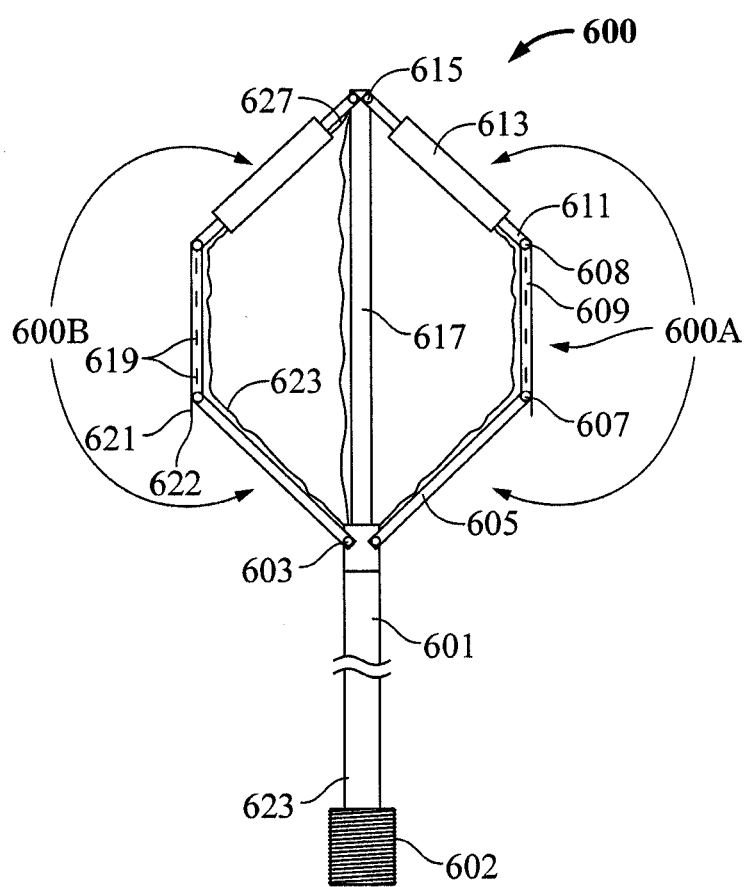
FIG. 7 illustrates an embodiment of a system for closing an aperture in a biological tissue having a frame in a deployed position and a sleeve in a first position.

Referring to FIG. 7, the sleeve deployment system may further include a retraction system. For example, the retraction system may include member 627 connected to the sleeve 613 such that pulling the member 627 returns the sleeve to the clip exposing position as shown in FIGS. 6A and 6B. The member 627 may include, for example, at least one cable, pushrod or other device for actuating the sleeve 613.

The sleeve positioning member 623 or member 627 may be slidably connected to the frame 600B members so that the sleeve positioning member 623 may follow the shape of the frame 600B in retracted or deployed position.

The at least one sleeve 613 may be disposed over the at least one distal member 611 when the frame 600B is in the deployed position, and disposed over at least one of the deployment arms 609 and/or hinge caps 621 when the frame 600B is in the retracted position.

Figure 8:
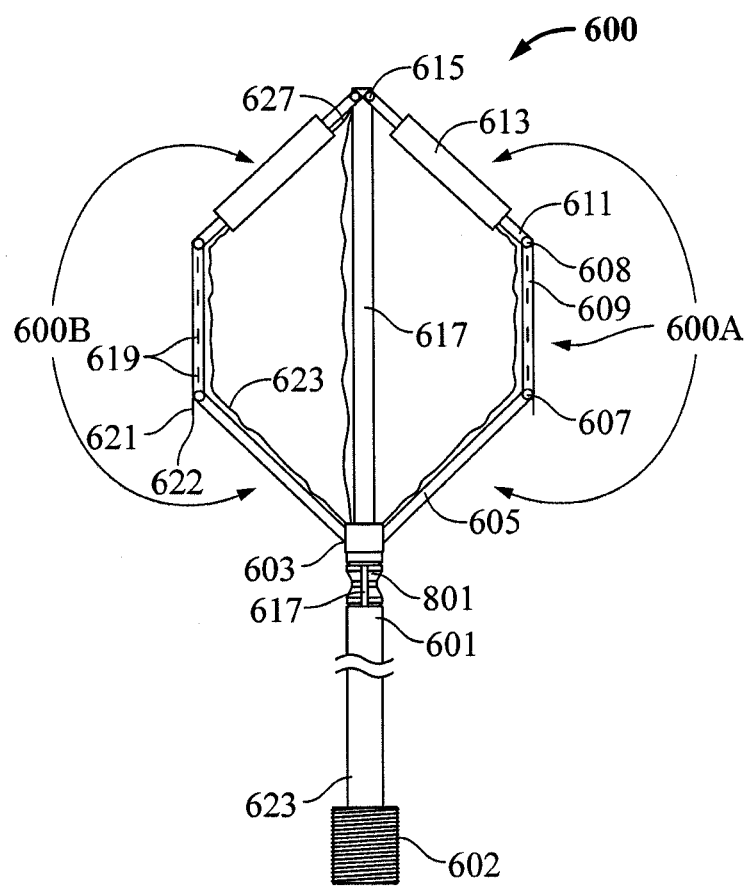
FIG. 8 illustrates an embodiment of a system for closing an aperture in a biological tissue having a frame in a deployed position and a sleeve in a first position.

Referring to FIG. 8, the sleeve deployment system may further include an articulation member 801 attaching the elongate shaft 601 to the proximal members 605. The actuation member 617 may slidably pass through the articulation member 801 from the elongate shaft 601 and attach to the distal members 611 such that distal sliding forces the system into the retracted position and proximal sliding forces the system into the deployed position.

Further described herein is a method for protecting tissue during a laparoscopic procedure, including providing a system 600 for closing an aperture in a biological tissue as described above, transitioning the frame 600B from the deployed position to the retained position, and causing the at least on sleeve 613 to be moved into the second position, i.e. positioned over at least one of the plurality of arms 609 and/or hinge covers 621 when the frame 600B is in either the retained or deployed position.

The method may further include expanding the frame 600B from the retracted state to the deployed state after inserting the system into the surgical site and exposing the plurality of clips 619.

The method may further include attaching a implant (as shown in FIG. 6) to the clips 619 before inserting the system 600 into the surgical site and expanding the frame 600B from the retained position to the deployed position after inserting the system 600 into the surgical site.

The method may further include placing the arms 609 on a desired location inside the surgical site and deploying an implant 650 from the system 600 to the desired location when the frame 600B is in the deployed position. In at least some embodiments, the transitioning step is done after the implant has been deployed.

The method may further include removing the system from the surgical site after causing the at least one sleeve 613 to be positioned over at least one of the plurality of arms 609 when the frame 600B is in the retained position.

The method may further comprise retracting the frame 600B to the retained position from the deployed position after deploying the implant 650, moving the at least one sleeve 613 into the second position after deployment of the implant 650, and removing the system 600 from the surgical site after moving the at least one sleeve 613 into the second position.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for closing an aperture in a biological tissue, the system comprising:
    a handle;
    an elongate shaft connected to the handle;
    a deployment scaffold connected to the elongate shaft, the deployment scaffold comprising a frame and a plurality of deployment arms hingedly connected to the frame, wherein the frame is configured to move from a retained position to a deployed position;
    a plurality of clips connected to the plurality of deployment arms, wherein the plurality of clips are configured to releasably retain a surgical implant; and
    a plurality of sleeves, each sleeve of the plurality of sleeves translatable along a single one of the deployment arms for selectively exposing or covering at least one of the plurality of clips when the frame is in the deployed position and the plurality of deployment arms are in an expanded configuration for releasing the surgical implant.

2. The system of claim 1, wherein at least one of the sleeves selectively covers at least one hinge connecting the plurality of deployment arms to the frame when the frame is in the retained position.

3. The system of claim 1, wherein at least one of the sleeves covers at least one of the plurality of clips when the frame is in one of the retained and deployed positions.

4. The system of claim 1, wherein at least one of the sleeves is made of a rigid material or semi-rigid material.

5. The system of claim 4, wherein the rigid or semi-rigid material comprises at least one material selected from the group consisting of a metal and a plastic.

6. The system of claim 1, wherein at least one if the sleeves comprises a flexible material.

7. The system of claim 6, wherein the flexible material comprises at least one of a fabric, a plastic, or a rubber.

8. The system of claim 1 further comprising at least one sleeve positioning member attached to at least one sleeve of the plurality of sleeves for translating the at least one sleeve along one of the deployment arms when the frame is in one of the retained and deployed positions.

9. The system of claim 1, wherein at least one proximal member attaches to the elongate shaft via an articulation member at a first hinge and to at least one of the plurality of deployment arms at a second hinge, wherein the at least one of the plurality of deployment arms is further connected to at least one distal member at a third hinge, and the at least one distal member is connected to an actuation member at a fourth hinge.

10. The system of claim 9, wherein at least one sleeve of a plurality of sleeves is capable of being disposed over the at least one distal member when the frame is in the deployed position, and disposed over at least one of the plurality of deployment arms when the frame is in the retained position.

11. The system of claim 9, further comprising a means for selectively disposing at least one sleeve of the plurality of sleeves over the at least one distal member and at least one of the plurality of deployment arms.

12. A method for protecting tissue during a laparoscopic procedure, comprising:
    providing a system for closing an aperture in a biological tissue, the system comprising:
        a handle;
        an elongate shaft connected to the handle;
        a deployment scaffold connected to the shaft, the deployment scaffold comprising a frame and a plurality of deployment arms hingedly connected to the frame, wherein the frame is configured to move from a retained position to at least one deployed position;
        a plurality of clips connected to the arms, wherein the clips are configured to releasably retain a surgical implant; and
        a plurality of sleeves, each sleeve of the plurality of sleeves translatable along a single one of the deployment arms for selectively exposing or covering at least one of the plurality of clips when the frame is in the deployed position and the plurality of deployment arms are in an expanded configuration for releasing the surgical implant;
    attaching an implant to the clips;
    transitioning the frame from the deployed position to the retained position;
    inserting the system into a surgical site;
    transitioning the frame from the retained position to the deployed position; and
    causing the at least one sleeve to be moved to a second position.

13. The method of claim 12, further comprising placing the arms on a desired location inside the surgical site and releasing the implant from the system to the desired location when the frame is in the deployed position.

14. The method of claim 13, further comprising removing the system from the surgical site after moving at least one sleeve of the plurality of sleeves into the second position.

15. A system for closing an aperture in a biological tissue, the system comprising:
    a handle;
    an elongate shaft connected to the handle;
    a deployment scaffold connected to the elongate shaft, the deployment scaffold comprising a frame and a plurality of deployment arms hingedly connected to the frame, wherein the frame is configured to move from a retained position to a deployed position;
    a plurality of clips connected to the plurality of deployment arms, wherein the plurality of clips are configured to releasably retain a surgical implant; and
    a plurality of sleeves, each sleeve of the plurality of sleeves translatable along a single one of the deployment arms when the frame is in the deployed position for selectively exposing or covering at least one of the plurality of clips.

\* \* \* \* \*